United States Patent
Ortiz et al.

(10) Patent No.: US 8,435,262 B2
(45) Date of Patent: May 7, 2013

(54) SUTURE MANAGEMENT

(75) Inventors: Mark S. Ortiz, Milford, OH (US);
Thomas E. Albrecht, Cincinnati, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 12/958,723

(22) Filed: Dec. 2, 2010

(65) Prior Publication Data

US 2011/0077671 A1  Mar. 31, 2011

Related U.S. Application Data

(62) Division of application No. 11/381,183, filed on May 2, 2006, now Pat. No. 7,862,582.

(51) Int. Cl.
*A61B 17/08* (2006.01)
*A61B 17/58* (2006.01)
*A61B 17/60* (2006.01)
*A61D 1/00* (2006.01)

(52) U.S. Cl.
USPC .............. 606/216; 242/375; 606/103

(58) Field of Classification Search .......... 606/103, 606/139, 140, 144, 146, 215, 216, 148; 242/160.1, 242/324.1, 324.2, 169, 370, 227, 410, 379, 242/376, 375–375.3, 419, 419.8, 419.9, 420.4, 242/382, 382.6, 396.4, 385; 206/63.3; 24/68 SK, 24/68 TT See application file for complete search history.

(56) References Cited

U.S. PATENT DOCUMENTS

| 871,345 | A | 11/1907 | Kleinshchmidt |
| 2,434,119 | A | 1/1948 | Nordmark |
| 2,550,927 | A | 5/1951 | Jurnove |
| 3,478,981 | A | 11/1969 | Barecki et al. |
| 3,569,674 | A | 3/1971 | Becker et al. |
| 3,628,751 | A | 12/1971 | Brauning et al. |
| 3,641,897 | A | 2/1972 | Fujimoto |

(Continued)

FOREIGN PATENT DOCUMENTS

| DE | 19847852 | 4/1999 |
| JP | 2001-520907 A | 11/2001 |

(Continued)

OTHER PUBLICATIONS

European Search Report dated Aug. 6, 2009; EP Application No. 07251823.6.

(Continued)

*Primary Examiner* — Dianne Dornbusch
(74) *Attorney, Agent, or Firm* — Nutter McClennen & Fish LLP (57) ABSTRACT

Various exemplary methods and devices are provided for tensioning suture. The methods and devices are particularly useful in surgical suturing applications in which it is desirable to maintain tension on suture being delivered, yet to allow the tension to be released as desired without retracting the suture. Thus, when tension is released, a length of suture extended from the device can remain extended without any tension being applied thereto. Tension is only applied to any additional length of suture that is extended from the device. The tension applied to the suture is proportional to the length of the suture extended from the device until the tension is released and reset.

13 Claims, 9 Drawing Sheets

U.S. PATENT DOCUMENTS

| | | | |
|---|---|---|---|
| 3,650,274 A * | 3/1972 | Edwards et al. | 606/233 |
| 3,654,702 A * | 4/1972 | Kelly, Jr. | 433/19 |
| 3,657,491 A | 4/1972 | Ryder et al. | |
| 3,834,048 A | 9/1974 | Maurer | |
| 3,865,329 A | 2/1975 | Higbee et al. | |
| 3,894,700 A | 7/1975 | Ito et al. | |
| 3,921,295 A * | 11/1975 | James | 433/21 |
| 3,997,130 A | 12/1976 | Policansky | |
| 4,003,270 A | 1/1977 | Moosberg | |
| 4,049,217 A | 9/1977 | Koopman | |
| 4,074,433 A | 2/1978 | Nelson | |
| 4,079,686 A | 3/1978 | Kasuga | |
| 4,264,302 A | 4/1981 | Wolk et al. | |
| 4,562,977 A | 1/1986 | Hollowell | |
| 4,577,807 A | 3/1986 | Urso | |
| 4,727,640 A | 3/1988 | Hollowell | |
| 4,830,307 A | 5/1989 | Lassi et al. | |
| 4,832,278 A | 5/1989 | Sugeta | |
| 4,841,888 A | 6/1989 | Mills et al. | |
| 4,901,938 A | 2/1990 | Cantley et al. | |
| 4,969,892 A * | 11/1990 | Burton et al. | 606/218 |
| 5,041,129 A | 8/1991 | Hayhurst et al. | |
| 5,076,510 A | 12/1991 | Norlander | |
| 5,080,299 A | 1/1992 | Gray et al. | |
| 5,080,663 A | 1/1992 | Mills et al. | |
| 5,114,090 A | 5/1992 | Lindblad | |
| 5,131,594 A | 7/1992 | Refior et al. | |
| 5,217,486 A | 6/1993 | Rice et al. | |
| 5,269,809 A | 12/1993 | Hayhurst et al. | |
| 5,292,249 A * | 3/1994 | German | 433/22 |
| 5,303,877 A | 4/1994 | Ciocca | |
| 5,376,101 A | 12/1994 | Green et al. | |
| RE34,941 E | 5/1995 | Gray et al. | |
| 5,437,681 A | 8/1995 | Meade et al. | |
| 5,443,218 A | 8/1995 | Ciocca | |
| 5,462,558 A | 10/1995 | Kolesa et al. | |
| 5,514,159 A | 5/1996 | Matula et al. | |
| 5,524,833 A | 6/1996 | Modinger et al. | |
| 5,540,705 A | 7/1996 | Meade et al. | |
| 5,571,119 A | 11/1996 | Atala | |
| 5,584,861 A | 12/1996 | Swain et al. | |
| 5,709,693 A | 1/1998 | Taylor | |
| 5,713,910 A | 2/1998 | Gordon et al. | |
| 5,732,611 A | 3/1998 | Voyer et al. | |
| 5,755,730 A | 5/1998 | Swain et al. | |
| 5,814,071 A | 9/1998 | McDevitt et al. | |
| 5,860,992 A | 1/1999 | Daniel et al. | |
| 5,887,594 A | 3/1999 | LoCicero, III | |
| 5,899,921 A | 5/1999 | Caspari et al. | |
| 5,902,321 A | 5/1999 | Caspari et al. | |
| 5,951,590 A * | 9/1999 | Goldfarb | 606/232 |
| 6,010,515 A | 1/2000 | Swain et al. | |
| 6,036,694 A | 3/2000 | Goble et al. | |
| 6,120,525 A * | 9/2000 | Westcott | 606/216 |
| 6,200,329 B1 | 3/2001 | Fung et al. | |
| 6,346,111 B1 | 2/2002 | Gordon et al. | |
| 6,358,259 B1 | 3/2002 | Swain et al. | |
| 6,390,404 B2 | 5/2002 | McCulloch | |
| 6,431,485 B2 | 8/2002 | Mitsuo et al. | |
| 6,443,962 B1 | 9/2002 | Gaber | |
| 6,454,778 B2 | 9/2002 | Kortenbach | |
| 6,463,986 B1 | 10/2002 | Gouda | |
| 6,494,888 B1 | 12/2002 | Laufer et al. | |
| 6,500,195 B2 | 12/2002 | Bonutti | |
| 6,506,196 B1 | 1/2003 | Laufer | |
| 6,524,328 B2 | 2/2003 | Levinson | |
| 6,540,789 B1 | 4/2003 | Silverman et al. | |
| 6,558,400 B2 | 5/2003 | Deem et al. | |
| 6,572,629 B2 | 6/2003 | Kalloo et al. | |
| 6,663,639 B1 | 12/2003 | Laufer et al. | |
| 6,694,643 B1 | 2/2004 | Hsu | |
| 6,719,763 B2 | 4/2004 | Chung et al. | |
| 6,745,969 B1 | 6/2004 | Gouda | |
| 6,746,460 B2 | 6/2004 | Gannoe et al. | |
| 6,755,843 B2 | 6/2004 | Chung et al. | |
| 6,773,440 B2 | 8/2004 | Gannoe et al. | |
| 6,773,441 B1 | 8/2004 | Laufer et al. | |
| 6,821,858 B2 | 11/2004 | Namatame et al. | |
| 6,835,200 B2 | 12/2004 | Laufer et al. | |
| 6,869,395 B2 | 3/2005 | Page et al. | |
| 6,908,427 B2 | 6/2005 | Fleener et al. | |
| 6,923,819 B2 | 8/2005 | Meade et al. | |
| 6,955,643 B2 | 10/2005 | Gellman et al. | |
| 6,966,518 B2 | 11/2005 | Kohlndorfer et al. | |
| 6,997,931 B2 | 2/2006 | Sauer et al. | |
| 7,033,370 B2 | 4/2006 | Gordon et al. | |
| 7,041,111 B2 | 5/2006 | Chu | |
| 7,060,077 B2 | 6/2006 | Gordon et al. | |
| 7,076,843 B2 | 7/2006 | Sakabayashi | |
| 7,251,966 B2 | 8/2007 | Fawcett et al. | |
| 7,255,111 B2 | 8/2007 | Chen | |
| 7,273,192 B2 | 9/2007 | Park | |
| 7,392,959 B2 | 7/2008 | Inuzuka et al. | |
| 7,455,681 B2 | 11/2008 | Wilke et al. | |
| 7,631,830 B2 | 12/2009 | Boelstler et al. | |
| 7,686,829 B2 | 3/2010 | Elliott et al. | |
| 7,862,582 B2 | 1/2011 | Ortiz et al. | |
| 2001/0023352 A1 | 9/2001 | Gordon et al. | |
| 2002/0193809 A1 | 12/2002 | Meade et al. | |
| 2003/0083674 A1 | 5/2003 | Gibbens | |
| 2003/0092969 A1 * | 5/2003 | O'Malley et al. | 600/216 |
| 2003/0109900 A1 | 6/2003 | Martinek | |
| 2003/0120265 A1 | 6/2003 | Deem et al. | |
| 2003/0171760 A1 | 9/2003 | Gambale | |
| 2003/0181924 A1 | 9/2003 | Yamamoto et al. | |
| 2003/0204195 A1 | 10/2003 | Keane et al. | |
| 2003/0225312 A1 | 12/2003 | Suzuki et al. | |
| 2003/0229296 A1 | 12/2003 | Ishikawa et al. | |
| 2003/0229361 A1 * | 12/2003 | Jackson | 606/144 |
| 2003/0233104 A1 | 12/2003 | Gellman et al. | |
| 2003/0233108 A1 | 12/2003 | Gellman et al. | |
| 2004/0002720 A1 | 1/2004 | Kortenbach et al. | |
| 2004/0006351 A1 | 1/2004 | Gannoe et al. | |
| 2004/0024386 A1 | 2/2004 | Deem et al. | |
| 2004/0034369 A1 | 2/2004 | Sauer et al. | |
| 2004/0059350 A1 | 3/2004 | Gordon et al. | |
| 2004/0082963 A1 | 4/2004 | Gannoe et al. | |
| 2004/0098050 A1 | 5/2004 | Foerster et al. | |
| 2004/0122452 A1 | 6/2004 | Deem et al. | |
| 2004/0122453 A1 | 6/2004 | Deem et al. | |
| 2004/0122473 A1 | 6/2004 | Ewers et al. | |
| 2004/0138682 A1 | 7/2004 | Onuki et al. | |
| 2004/0147941 A1 | 7/2004 | Takemoto et al. | |
| 2004/0147958 A1 | 7/2004 | Lam et al. | |
| 2004/0162568 A1 | 8/2004 | Saadat et al. | |
| 2004/0172047 A1 | 9/2004 | Gellman et al. | |
| 2004/0193184 A1 | 9/2004 | Laufer et al. | |
| 2004/0193187 A1 * | 9/2004 | Boehringer et al. | 606/144 |
| 2004/0194790 A1 | 10/2004 | Laufer et al. | |
| 2004/0210243 A1 | 10/2004 | Gannoe et al. | |
| 2004/0215058 A1 | 10/2004 | Zirps et al. | |
| 2004/0260344 A1 | 12/2004 | Lyons et al. | |
| 2005/0015101 A1 | 1/2005 | Gibbens et al. | |
| 2005/0033319 A1 | 2/2005 | Gambale et al. | |
| 2005/0055038 A1 | 3/2005 | Kelleher et al. | |
| 2005/0070931 A1 | 3/2005 | Li et al. | |
| 2005/0075653 A1 | 4/2005 | Saadat et al. | |
| 2005/0075654 A1 | 4/2005 | Kelleher | |
| 2005/0085851 A1 | 4/2005 | Fiehler et al. | |
| 2005/0090827 A1 * | 4/2005 | Gedebou | 606/72 |
| 2005/0131430 A1 | 6/2005 | Ravikumar | |
| 2005/0143760 A1 | 6/2005 | Imran | |
| 2005/0143762 A1 | 6/2005 | Paraschac et al. | |
| 2005/0149067 A1 | 7/2005 | Takemoto et al. | |
| 2005/0165419 A1 | 7/2005 | Sauer et al. | |
| 2005/0192599 A1 | 9/2005 | Demarais | |
| 2005/0192601 A1 | 9/2005 | Demarais | |
| 2005/0203488 A1 | 9/2005 | Michlitsch et al. | |
| 2006/0058842 A1 * | 3/2006 | Wilke et al. | 606/213 |
| 2006/0095076 A1 * | 5/2006 | Elliott et al. | 606/216 |
| 2006/0195121 A1 | 8/2006 | Chu | |
| 2007/0199635 A1 | 8/2007 | McCauley et al. | |

FOREIGN PATENT DOCUMENTS

| | | |
|---|---|---|
| JP | 2005-523103 A | 8/2005 |
| WO | 9519140 A1 | 7/1995 |
| WO | 99/35974 A1 | 7/1999 |

| | | | |
|---|---|---|---|
| WO | 0018307 | | 4/2000 |
| WO | 0061012 | A1 | 10/2000 |
| WO | 0110312 | A1 | 2/2001 |
| WO | 0166001 | A2 | 9/2001 |
| WO | 01/76895 | A1 | 10/2001 |
| WO | 0189393 | A1 | 11/2001 |
| WO | 0217077 | A1 | 2/2002 |
| WO | 02096327 | A2 | 12/2002 |
| WO | 2004021894 | A1 | 3/2004 |
| WO | 2005034729 | A2 | 4/2005 |

OTHER PUBLICATIONS

Extended European Search Report issued Nov. 4, 2008 for Application No. 07251823.6 (6 Pages).

Japanese Office Action issued Feb. 21, 2012 for Application No. 2007-121053 (2 Pages).

* cited by examiner

SUTURE MANAGEMENT

CROSS REFERENCE TO RELATED APPLICATIONS

This application is a divisional of U.S. application Ser. No. 11/381,183 filed on May 2, 2006 (now U.S. Pat. No. 7,862,582) and entitled "Suture Management," which is hereby incorporated by reference in its entirety.

FIELD OF THE INVENTION

The present invention relates to method and devices for maintaining tension on a length of suture.

BACKGROUND

Severe obesity is a major health risk that can decrease life expectancy and give rise to a number of other associated ailments, including the onset of cardiovascular disease, hypertension, diabetes and severe arthritis. A number of surgical procedures can be performed to aid in the treatment of obesity. The most common procedure is a gastric restriction procedure in which opposed gastric walls are fastened or stapled together to effectively reduce the volume of a patient's stomach. More specifically, the stomach is divided by a series of staples or fasteners that extend vertically for about 2.5 inches to create a smaller stomach pouch. The outlet of the pouch into the larger stomach limits the amount of food the stomach can hold and reduces the rate of gastric emptying.

Some gastric restriction procedures utilize a series of fasteners that are coupled by a suture used to cinch and pull the fastened tissue together. Suture-coupled fasteners offer the advantage of allowing the fasteners to be applied to each wall of the stomach separately, and then to be cinched together using the suture after the fastener applying device is removed. In order to apply staples, on the other hand, folds must be created in each wall to engage and pull the tissue together, thus requiring that the staples be inserted through four walls of tissue.

While suture-coupled fasteners tend to be more advantageous than staples, slack or loops of excess suture can form as the surgeon is attaching the fasteners to the opposed walls of the stomach. For the gastric restriction procedure to be successful, the suture must be tightly cinched to pull the gastric walls together so that the reduced volume of the patient's stomach can be maintained. If any slack or loose loops of suture are present, the stomach will expand and the restriction procedure will not be effective. Thus, the surgeon must manually maintain tension on the suture as the fasteners are being applied. This can be difficult though, as most fastener delivery devices tend to require two hands to operate.

Accordingly, a need exists for devices and techniques for tensioning a length of suture.

SUMMARY

Methods and devices are provided for tensioning a length of suture. In one embodiment, a suture tensioning device is provided having a spool disposed around a hub, a biasing element associated with the spool, and a wheel disposed around the spool and having a suture wound there around. The wheel is movable between an engaged position in which the wheel rotates with the spool such that the biasing element biases the spool to maintain tension on the suture, and a disengaged position in which the spool rotates independent of the wheel to release the tension applied to the suture.

While various techniques can be used to move the wheel between the engaged and disengaged positions, in one embodiment the wheel can be configured to slide laterally relative to the spool to move between the engaged and disengaged positions. The spool can include opposed flanges formed around opposed side edges thereof, and the wheel can be movable laterally between the opposed flanges. The device can also include a release mechanism that is movable between a first position in which the release mechanism biases the wheel toward the spool into the engaged position, and a second position in which the release mechanism is spaced apart from the wheel to allow the wheel to move to the disengaged position. The release mechanism can be, for example, a clip having protrusions formed on opposed ends. The protrusions can be positioned between the wheel and the spool when the clip is in the first position, and they can be spaced apart from the wheel and the spool when the clip is in the second position. In an exemplary embodiment, the clip is movably disposed around a housing disposed around the wheel and spool and containing the hub therein, and the protrusions on the opposed ends of the clip can extend into openings formed in the housing.

The device can also include at least one engagement mechanism formed on the wheel and the spool for mating the wheel and the spool when the wheel is in the engaged position. The engagement mechanism can be, for example, at least one tooth formed on at least one of the wheel and the spool, and a plurality of teeth formed on the other one of the wheel and the spool. The teeth can positioned to engage one another when the release mechanism biases the wheel toward the spool.

The biasing element can also have a variety of configurations, and in one embodiment the biasing element can be a spring disposed between the hub and the spool. The spring can have a first end coupled to the hub and a second end coupled to the spool. The hub can be formed within a housing disposed around the wheel and having an opening formed therein for receiving the suture therethrough.

In another embodiment, a suture application and management kit is provided and includes a suturing device configured to deliver a suture to a surgical site, and a suture tensioning device configured to apply tension to the suture as the suture is extended from the suture tensioning device. The suture tensioning device can also include a release mechanism that is effective to release the tension applied to the suture without further extending the suture. While various suturing devices can be used, in one embodiment the suturing device can include an end effector configured to apply at least one fastener to tissue. The suture can be coupled to the fastener(s). The suture tensioning device can optionally be configured to couple to the suturing device.

Suture tensioning methods are also provided, and in one embodiment the method can include extending a first length of suture from a suture management device. The suture management device can apply tension to the first length of suture as the suture is extended. The method can further include actuating a release mechanism on the suture management device to release the tension applied to the first length of suture without further extending the suture. In a further embodiment, after actuating the release mechanism, a second length of suture can be extended from the suture management device, and the suture management device can apply tension to the second length of suture as the second length of suture is extended. The tension applied to the second length of suture is preferably proportional to a length of the second length of suture.

In another embodiment, the suture management devices can include a spring-loaded spool and a wheel disposed around the spool and having the suture wound there around, and extending the suture can rotate the wheel and spool to load the spring-loaded spool such that tension is applied to the suture. Actuating the release mechanism can also be effective to cause the wheel to disengage from the spring-loaded spool to allow the spring-loaded spool to unwind and release the tension on the suture without further extending the suture. The method can also include delivering a leading end of the suture to a surgical site, and optionally applying at least one fastener having the suture coupled thereto to tissue.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for tensioning suture. The methods and devices are particularly useful in surgical suturing applications in which it is desirable to maintain tension on suture being delivered, yet to allow the tension to be released as desired without retracting the suture. Thus, when tension is released, a length of suture extended from the device can remain extended without any tension being applied thereto. Tension is only applied to any additional length of suture that is extended from the device. The tension applied to the suture is proportional to the length of the suture extended from the device until the tension is released and reset.

Figure 1A:
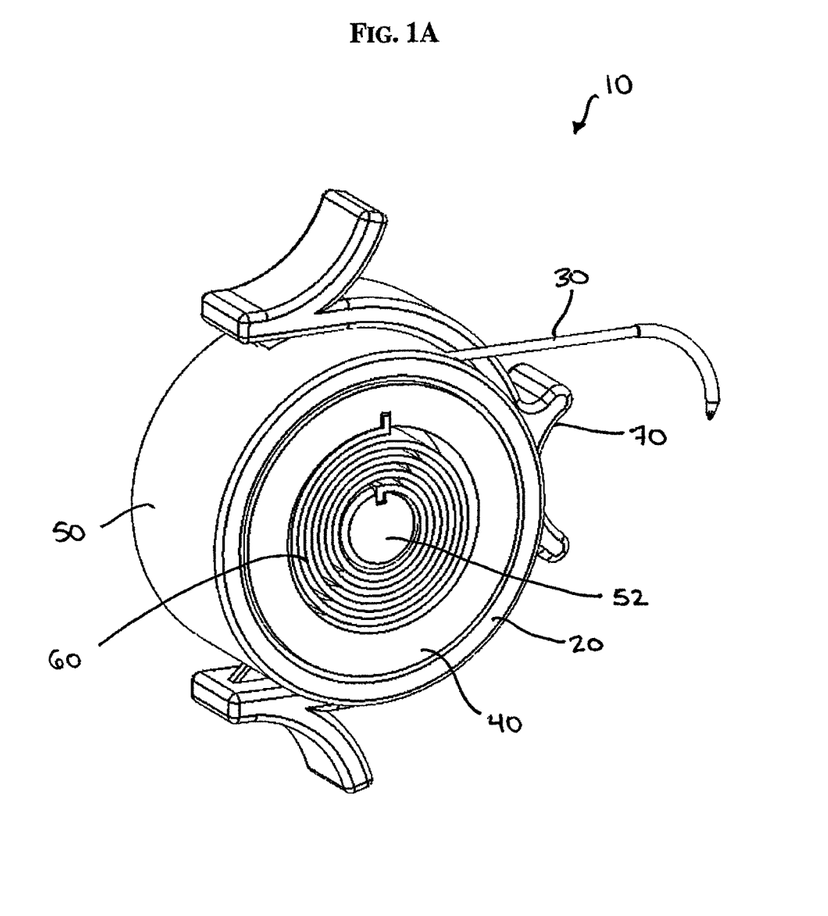
FIG. 1A is side view of one exemplary embodiment of a suture management device.
Figure 1B:
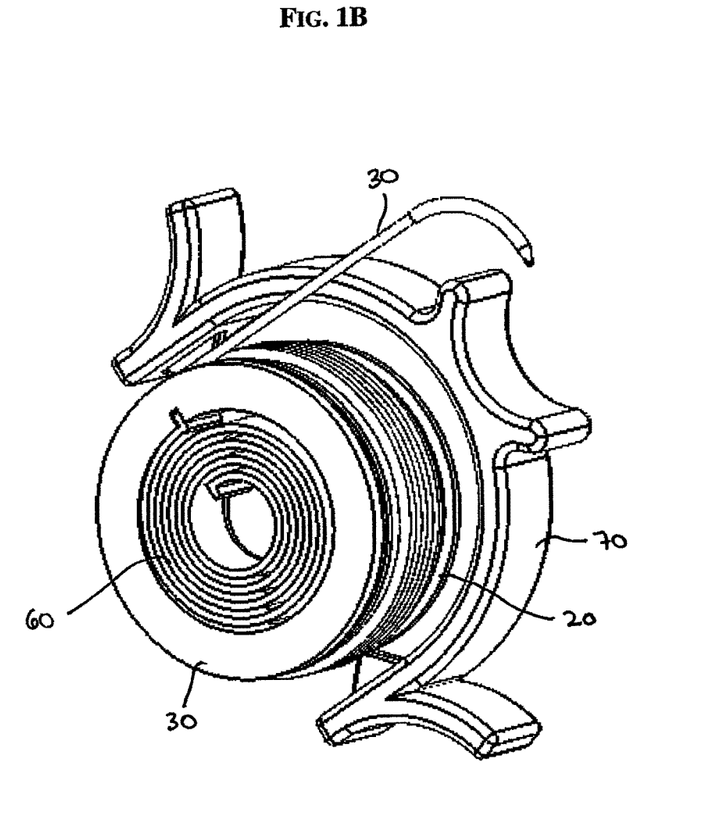
FIG. 1B is a side perspective view of the device of FIG. 1A showing a housing removed from the device.
Figure 1C:
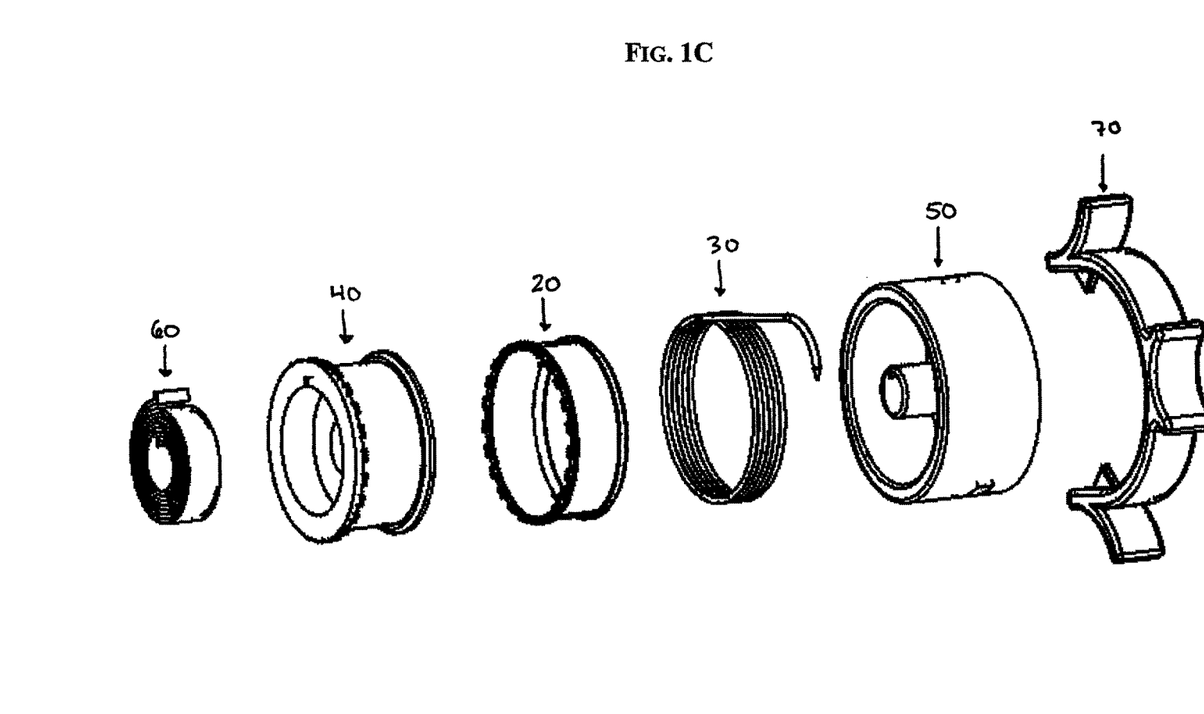
FIG. 1C is an exploded view of the device of FIG. 1A.

FIGS. 1A-1C illustrate one exemplary embodiment of a suture management device 10. As shown, the device 10 generally includes a wheel 20 having a suture 30 disposed there around. The wheel 20 is rotatably mounted on a spool 40, which is disposed within a housing 50. The housing 50 includes a central hub 52 formed therein, and a biasing element 60 disposed around the central hub 52 and disposed within the spool 40. The biasing element 60 is coupled between the central hub 52 and the spool 40 such that the biasing element 60 applies a force to the spool 40 as the spool 40 is rotated within the housing 50. In use, the wheel 20 is movable between an engaged position in which the wheel 20 rotates with the spool 30 such that the biasing element 60 biases the spool 40 to maintain tension on the suture 30, and a disengaged position in which the spool 40 can rotate independent of the wheel 20 to release the tension applied to the suture 30 extended from the device 10. The device 10 can also include a release mechanism 70 that is movable between a first position in which the release mechanism 70 biases the wheel 20 toward the spool 30 into the engaged position, and a second position in which the release mechanism 70 is spaced apart from the wheel 20 to allow the wheel 20 to move to the disengaged position.

Figure 2A:
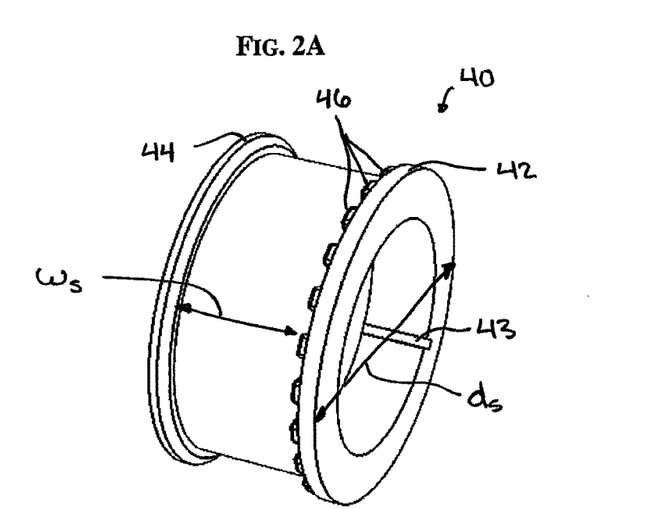
FIG. 2A is a perspective view of a spool of the device of FIGS. 1A-1C.
Figure 2B:
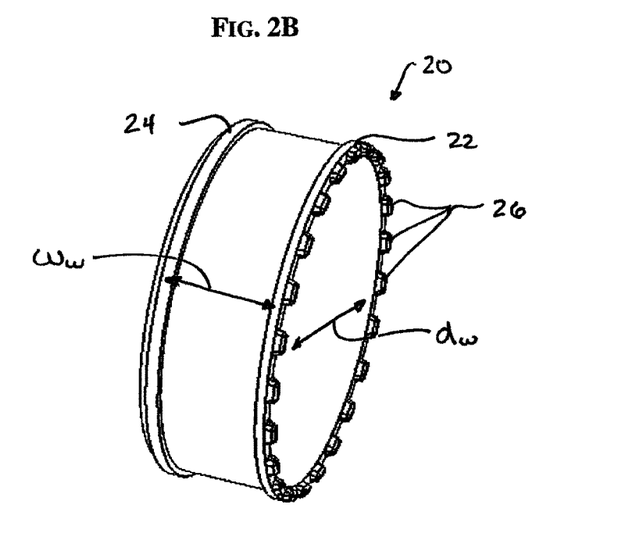
FIG. 2B is a perspective view of a wheel of the device of FIGS. 1A-1C.

The spool 40 and wheel 20 are shown in more detail in FIGS. 2A and 2B, respectively. In general, the spool 40 and wheel 20 are each in the form of a hollow cylindrical member. The wheel 20 has an inner diameter $d_w$ that is only slightly larger than an outer diameter $d_s$ of the spool 40 such that the wheel 20 can be rotatably disposed around and in contact with the spool 40. The wheel 20 also has a width $w_w$ that is configured to seat a suture wound there around, preferably multiple times. The width $w_w$ of the wheel 20 is also preferably less than a width $w_s$ of the spool 40 to allow the wheel 20 to slide laterally relative to the spool 40 between an engaged position, in which the wheel 20 is engaged with and rotates with the spool 40, and a disengaged position, in which the wheel 20 and spool 40 can rotate independent of one another, as will be discussed in more detail below. The wheel 20 and the spool 40 can also include other features to facilitate positioning of the wheel 20 around the spool 40. For example, FIG. 2A illustrates opposed flanges 42, 44 formed around opposed side edges of the spool 40. The wheel 20 can thus slide laterally between the opposed flanges 42, 44 without sliding off of the spool 40. The wheel 20 can also include opposed flanges 22, 24 formed thereon. However, the flanges 22, 24 on the wheel 20 can be configured to facilitate positioning of the suture around the wheel 20, and in particular to prevent the suture from sliding off of the wheel 20 and winding directly around the spool 40.

Figure 2C:
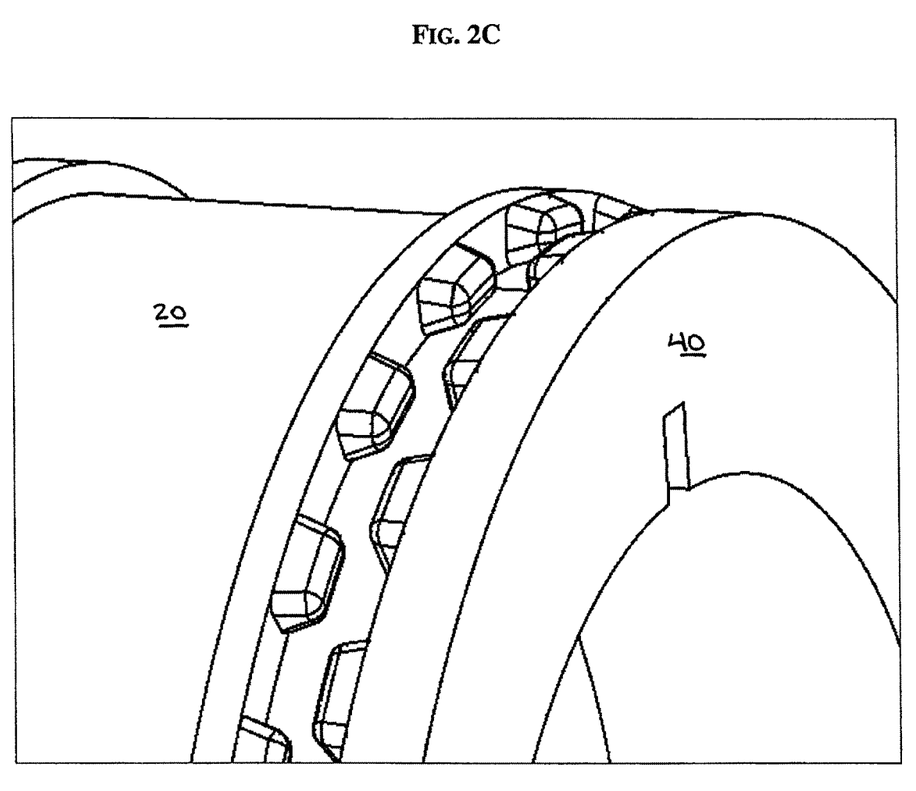
FIG. 2C is an enlarged view of the wheel of FIG. 2B disposed on the spool of FIG. 2A, showing the wheel in a disengaged position.
Figure 3:
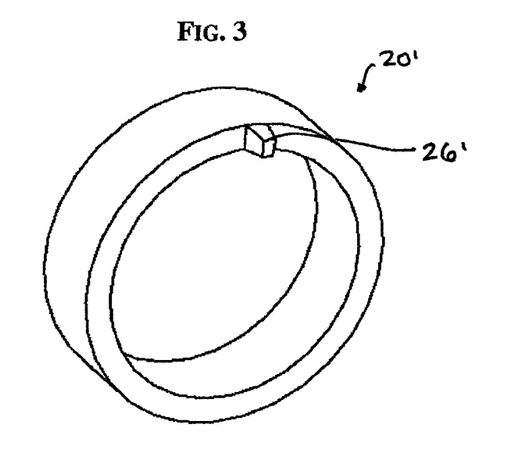
FIG. 3 is a perspective view of another embodiment of a wheel for use with the device of FIGS. 1A-1C.

As mentioned above, the wheel 20 can slide laterally on the spool 40 to move between an engaged position and a disengaged position. Various techniques can be used to mate the wheel 20 and spool 40 when the wheel 20 is in the engaged position. As shown in FIGS. 2A and 2B, the wheel 20 and the spool 40 each include a plurality of teeth 26, 46 formed thereon. In particular, the spool 40 includes a plurality of teeth 46 formed on an inner-facing surface of one of the flanges, e.g., flange 42, and the wheel 20 includes a plurality of teeth 26 formed on an outer facing edge of one of the flanges, e.g., flange 22. The teeth 26 on the wheel 20 are configured to be received between the teeth 46 on the spool 40. While multiple teeth are shown on the wheel 20 and spool 40, one of the members, e.g., the wheel 20, can include a single tooth, and the other member, e.g., the spool 40, can include a plurality of teeth. By way of non-limiting example, FIG. 3 illustrates an alternative embodiment of a wheel 20' having a single tooth 26' formed on an outer edge thereof. In use, when the wheel 20 is slid laterally on the spool 40 to position the teeth 26 on the wheel 20 between and in engagement with the teeth 46 on the spool 40, the wheel 20 and spool 40 will rotate together such that tension is applied to any length of suture extended from the wheel 20. When the wheel 20 is moved to the disengaged position, as shown in FIG. 2C, the wheel 20 and spool 40 can rotate independently, thus allowing the tension on a length of suture extended from the wheel 20 to be released and reset. Exemplary techniques for moving the wheel 20 between the engaged and disengaged positions will be discussed in more detail below with respect to FIG. 7.

Figure 4:
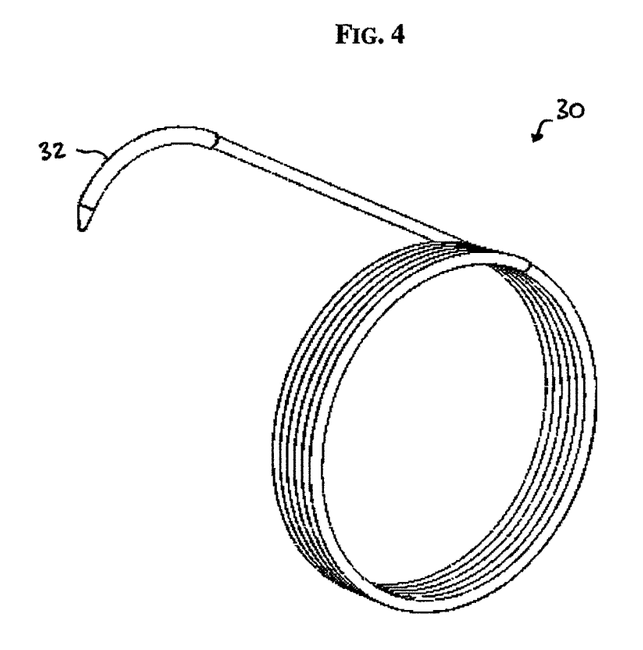
FIG. 4 is a perspective view of a suture and needle of the device of FIGS. 1A-1C.

The suture 30 which is disposed around the wheel 20 can have various configurations and it can include a leading end that is configured to be applied directly to tissue, or that is configured to couple to another device or an implant, such as a fastener. FIG. 4 illustrates one exemplary embodiment of a suture 30 which is configured to be wound around the wheel 20. A needle 32 is shown coupled to a leading end of the suture 30 for suturing tissue. While not shown, in other embodiments the suture 30 can be coupled directly to a suturing device.

In order to apply tension to a length of suture extended from the wheel 20, the device 10 can include a biasing element that is coupled to the spool 40 and that is configured to apply a biasing force to the spool 40 as the spool 40 and wheel 20 are rotated. While various biasing techniques can be used, in one exemplary embodiment the biasing element can be coupled between the housing 50 and the spool 40. The housing 50 is shown in more detail in FIG. 5, and as shown the housing 50 has a generally cylindrical configuration with a hollow interior that receives the wheel 20, spool 40, and biasing element. A central hub 52 is disposed in the housing 50, and it is configured to seat the biasing element there around. One exemplary biasing element 60 is shown in more detail in FIG. 6, and as shown the biasing element 60 is in the form of a constant force spring that is coiled and includes a first inner end 62 and a second outer end 64. The first inner end 62 is configured to couple to the hub 52. Referring back to FIG. 5, the hub 52 includes a slot 53 formed therein for receiving a bent portion on the first inner end 62 of the biasing element 60. Other mating techniques, such as adhesives, welding, etc., can be used to mate the first inner end 62 of the biasing element 60 to the hub 52. While the biasing element 60 is disposed around the hub 52, it is also disposed within the spool 40. Thus, the second outer end 64 of the biasing element 60 can mate to an inner surface of the spool 40. Referring back to FIG. 2A, the spool 40 includes a slot 43 formed therein for receiving a bent portion on the second outer end 64 of the biasing element 60. Again, other mating techniques, such as adhesives, welding, etc., can be used to mate the second outer end 64 of the biasing element 60 to the spool 40.

Since the biasing element 60 is mated between the hub 52 on the housing 50 and the spool 40, rotation of the spool 40 will cause the biasing element 60 to wind up and tighten. As a result, the biasing element 60 will apply a biasing force to the spool 40. Thus, when the suture 30 disposed around the wheel 20 is extended from the device 10, and the wheel 20 is in the engaged position such that the spool 40 rotates with the wheel 20, the biasing element 60 will apply tension to the suture 30. The tension will be substantially proportional to the length of suture 30 extended from the device 10. When the wheel 20 is moved to the disengaged position, the spool 40 is free to rotate relative to the wheel 20. The biasing element 60 will thus cause the spool 40 to free spin and return to its original position, such that the biasing element 60 is in a resting state and no tension is applied to the suture 30 that is extended from the device 10. When the wheel 20 is moved back into the engaged position, tension will only be applied to additional lengths of suture extended from the device 10. Thus, the user can release the tension at any time during use of the device 10 to release a predetermined amount of suture.

Figure 5:
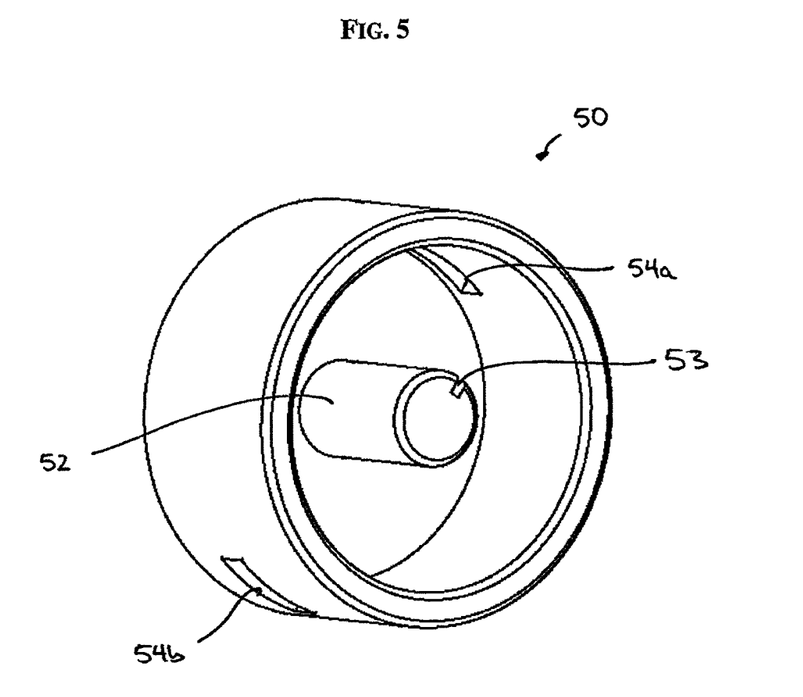
FIG. 5 is a perspective view of a housing of the device of FIGS. 1A-1C.
Figure 6:
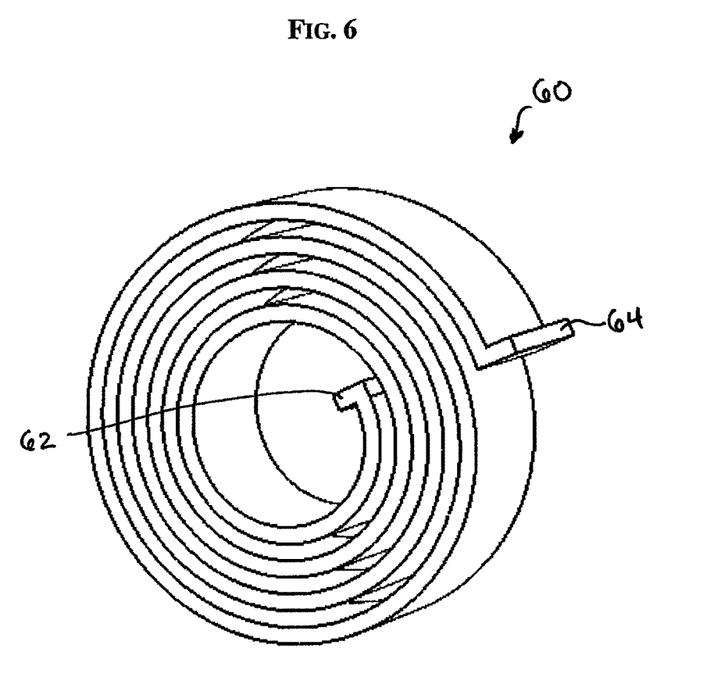
FIG. 6 is a perspective view of a biasing element of the device of FIGS. 1A-1C.
Figure 7:
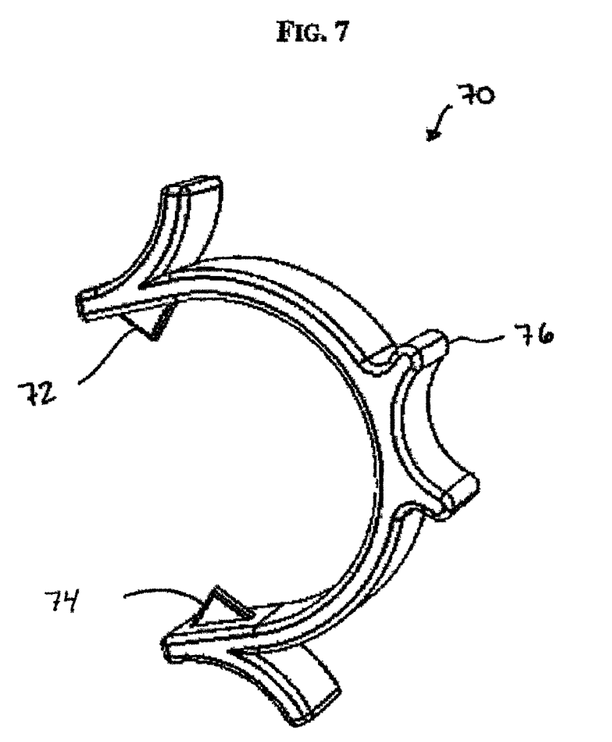
FIG. 7 is a perspective view of a release mechanism of the device of FIGS. 1A-1C.

In order to move the wheel 20 between the engaged and disengaged positions, the device 10 can include a release mechanism that is coupled to the housing. FIG. 7 illustrates one exemplary embodiment of a release mechanism in the form of a clip 70 that extends around a portion of the housing 50. The clip 70 includes opposed protrusions 72, 74 that extend into opposed openings 54a, 54b formed in the housing 50. The openings 54a, 54b in the housing 50 are shown in FIG. 5, and as shown they are positioned on opposite sides of the housing 50. Each opening 54a, 54b can have a generally elongate shape to allow the protrusions 72, 74 formed on the clip 70 to slidably move within the openings 54a, 54b. In use, the clip 70 can be press-fit around the housing 50 such that the protrusions 72, 74 are positioned within the openings 54a, 54b to mate the clip 70 to the housing 50. The clip 70 can slide toward and away from the housing 50 between first and second positions to move the wheel 20 between the engaged and disengaged positions. In particular, when the clip 70 is positioned a distance apart from the housing 50, such that the protrusions 72, 74 are pulled to one side of the openings 54a, 54b, the protrusions 72, 74 will not contact the wheel 20 and spool 40, allowing the wheel 20 to remain in the disengaged position, in which the wheel 20 rotates independent of the spool 40. When the clip 70 is moved toward the housing 50, the protrusions 72, 74 slide toward the other end of the openings 54a, 54b and are wedged between the wheel 20 and the spool 40. In an exemplary embodiment, the protrusions 72, 74 extend between the wheel 20 and the spool 40 on the opposite side of the teeth 26, 46 on the wheel 20 and the spool 40. As a result of the protrusions 72, 74 being wedged between the wheel 20 and the spool 40, the wheel 20 is forced into the engaged position, in which the wheel 20 and spool 40 must rotate together. In other words, when the clip 70 is moved toward the housing 50, the clip 70 locks the teeth 26, 46 on the wheel 20 and spool 40. When the clip 70 is released and moved away from the housing 50, the wheel 20 is free to move away from the spool 40 to the disengaged position. The orientation of the teeth 26, 46 on the wheel and/or spool 40 can optionally facilitate movement of the wheel 20 away from the spool 40 when the clip 70 is released. For example, the teeth 26, 46 can be angled or can taper, as shown in FIG. 2C, such that tension applied to the suture 30 disposed around the wheel 20 will pull the wheel 20 away from and out of engagement with the spool 40. In other embodiments, a biasing element can be used to bias the wheel 20 to the disengaged position, so that the wheel 20 automatically returns to the disengaged position when the clip 70 is released. The clip 70 can also include a biasing element that biases the clip 70 into engagement with the housing 50, such that the wheel 20 is held in the engaged position. A person skilled in the art will appreciate that a variety of other techniques can be used to move the wheel 20 between the engaged and disengaged positions, to thereby release tension applied to a length of suture extended from the device 10. As further shown in FIG. 7, the clip 70 can also include other features such as a handle 76 to facilitating grasping and movement of the clip 70 between the first and second positions.

The suture tensioning device can be used in a variety of surgical applications, and it can apply tension to a suture being directly implanted in tissue, or it can apply tension to a suture being used with various other devices. For example, the suture extended from the device can be coupled, directly or via another suture, to a fastener, such as a surgical clip. The suture can also extend through, or be coupled to a suture that extends through, a fastener applying device, such as a surgical clip applier. The suture tensioning device can also be mounted on or formed integrally with a variety of surgical suturing devices.

In use, as the suture 30 is delivered to a surgical site, a length of suture will be extended from the device 10. With the wheel 20 in the engaged position, the wheel 20 will rotate with the spool 40 as the suture 30 is extended. The biasing element 60 will thus apply tension to the spool 40, which is transferred to the suture 30, thereby keeping the suture 30 taught. This is particularly advantageous as it will prevent knots or kinks from being formed in the suture 30. When the surgeon needs to release the tension, the release mechanism, e.g., the clip 70, can be pulled away from the housing 50 to release the wheel 20. The wheel 20 can thus slide out of engagement with the spool 40, leaving the spool 40 free to rotate until the biasing element 60 is in its initial, resting configuration. As a result, no tension is applied to the length of suture that is extended from the device 10. When the clip 70 is moved back toward the housing 50 to move the wheel 20 to the engaged position, tension will be applied only to any additional length of suture that is extended from the device 10.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A suture tensioning method, comprising:
    extending a first length of suture from a suture management device, the suture management device applying tension to the first length of suture as the suture is extended;
    delivering a leading end of the suture to a surgical site; and
    actuating a release mechanism on the suture management device to release the tension applied to the first length of suture without further extending the suture.

2. The method of claim 1, further comprising, after actuating the release mechanism, extending a second length of the suture from the suture management device, the suture management device applying tension to the second length of the suture as the second length of the suture is extended, wherein the tension applied to the second length of the suture is proportional to a length of the second length of the suture.

3. The method of claim 1, wherein the suture management devices includes a spring-loaded spool and a wheel disposed around the spool and having the suture wound there around, and wherein extending the suture rotates the wheel and spool to load the spring-loaded spool such that tension is applied to the suture.

4. The method of claim 3, wherein actuating the release mechanism causes the wheel to disengage from the spring-loaded spool to allow the spring-loaded spool to unwind and release the tension on the suture without further extending the suture.

5. The method of claim 3, further comprising, after actuating the release mechanism, extending a second length of suture from the suture management device, which causes the wheel to rotate independent from the spool.

6. The method of claim 1, wherein delivering the leading end of the suture to a surgical site further comprises applying at least one fastener to tissue, the suture being coupled to the at least one fastener.

7. A suture tensioning method, comprising:
    extending a first length of suture from a suture management device, the suture being wound around a wheel that is in direct engagement with a spool in the suture management device, and the suture management device applying tension to the first length of suture as the suture is extended; and
    actuating a release mechanism on the suture management device to move the wheel laterally out of direct engagement with the spool such that the spool rotates independent of the wheel to thereby release the tension applied to the first length of suture.

8. The method of claim 7, wherein the spool is spring-loaded such that extending the first length of suture simultaneously rotates the wheel and spool to load the spool and thereby apply tension to the first length of suture.

9. The method of claim 7, further comprising delivering a leading end of the first length of suture into tissue.

10. A suture tensioning method, comprising:
    extending a length of suture from a suture management device, the suture being disposed around a wheel that rotates when the length of suture is extended from the suture management device, and the suture management device having a biasing element that applies a force to the wheel to tension the length of suture as the suture is extended;
    actuating a release mechanism on the device to release the tension applied to the wheel by the biasing element, thereby releasing the tension applied to the suture while the length of suture extending from the suture management device remains unchanged.

11. The method of claim 10, wherein the wheel remains stationary when the release mechanism is actuated.

12. The method of claim 10, further comprising delivering a needle on a leading end of the length of suture into tissue.

13. The method of claim 10, wherein actuating the release mechanism moves the wheel laterally.

* * * * *